United States Patent [19]

Keller

[11] Patent Number: 5,336,832
[45] Date of Patent: Aug. 9, 1994

[54] RECOVERY OF HF FROM HYDROCARBON STREAMS

[75] Inventor: Alfred E. Keller, Ponca City, Okla.

[73] Assignee: Conoco Inc., Ponca City, Okla.

[21] Appl. No.: 972,664

[22] Filed: Nov. 6, 1992

[51] Int. Cl.$^5$ ............................. C07C 2/60; C07C 2/62
[52] U.S. Cl. ................................ 585/710; 585/723; 585/800; 585/868; 502/22
[58] Field of Search ............... 585/710, 723, 800, 868; 502/22, 24

[56]  References Cited

U.S. PATENT DOCUMENTS

| | | |
|---|---|---|
| 2,419,558 | 4/1947 | Gibson . |
| 3,101,254 | 8/1963 | Cunningham . |
| 3,140,152 | 7/1964 | Rucker et al. . |
| 3,157,469 | 11/1964 | Tufts . |
| 3,219,410 | 11/1965 | Dexter et al. . |
| 3,258,308 | 6/1966 | Peterson et al. . |
| 3,314,755 | 4/1967 | Claus . |
| 3,551,098 | 12/1970 | Flemmert . |
| 3,711,596 | 1/1973 | Hartig . |
| 3,798,875 | 3/1974 | Morris . |
| 3,976,447 | 8/1978 | Merchant et al. . |
| 4,069,268 | 1/1978 | Siskin et al. ............... 585/375 |
| 4,094,924 | 6/1978 | Siskin et al. ............... 585/725 |
| 4,096,199 | 6/1978 | Green et al. ............... 502/22 |
| 4,199,409 | 4/1980 | Skraba . |
| 4,777,323 | 10/1988 | Hann et al. ............... 585/723 |

FOREIGN PATENT DOCUMENTS

| | | |
|---|---|---|
| 1073453 | 1/1960 | Fed. Rep. of Germany . |
| 1075567 | 2/1960 | Fed. Rep. of Germany . |
| 1181178 | 11/1964 | Fed. Rep. of Germany . |

Primary Examiner—Anthony McFarlane
Attorney, Agent, or Firm—William D. Hall

[57] ABSTRACT

Refining processes for recovering HF from acid soluble oils (ASO) generated by the HF recovery unit of an HF alkylation unit are provided. ASO containing HF is removed from the HF recovery unit and contacted with water to form a system having two phases, an aqueous HF containing phase and an organic phase. After phase separation, the aqueous HF containing phase passes through a bed of fluidized NaF crystals, where the NaF reacts with the HF to form salts having the general formula NaF.nHF. Flow of the aqueous HF containing phase to the bed continues until exhaustion of the bed, as determined by the detection of HF in the effluent. After exhaustion of the bed, the process provides for the regeneration of the bed and release of anhydrous HF which is then returned to the HF alkylation unit.

26 Claims, 1 Drawing Sheet

RECOVERY OF HF FROM HYDROCARBON STREAMS

BACKGROUND AND SUMMARY OF THE INVENTION

SUMMARY OF THE INVENTION

This invention provides a method for recovering residual hydrogen fluoride (HF) from hydrocarbon streams produced by an HF alkylation unit.

BACKGROUND OF THE INVENTION

The alkylation of olefins provides important blending stocks for the manufacture of gasoline. In a typical alkylation process, olefins such as propylene or butylene react with a branched alkane such as isobutane in the presence of a catalyst to produce a branched chain paraffin in the gasoline boiling range. These branched hydrocarbons are blended with gasoline in order to improve the final octane number.

One commonly used catalyst for this reaction is hydrogen fluoride (HF). The alkylation reaction is carried out in an HF alkylation unit which typically consists of three major units: 1. reactor/settler, 2. product fractionation and treating, and 3. acid regeneration unit. While the majority of the HF reprocessed in the acid regeneration unit is returned to the acid settler/reactor unit, a portion is lost to the bottom waste product of the regeneration unit, known as acid soluble oils (ASO).

The toxicity of HF necessitates disposal of the ASO containing HF in a manner precluding direct release of HF to the environment. Common disposal methods include incineration of the ASO containing HF or neutralization of the ASO containing HF with caustic, followed by treatment of the spent caustic solution with an inorganic calcium salt in order to precipitate out calcium fluoride which is further dewatered, neutralized and landfilled. Alternatively, the ASO containing HF may be treated directly with an inorganic calcium salt such as $CaCl_2$ to precipitate $CaF_2$ which may then be separated and landfilled.

In view of the health and environmental hazards associated with the disposal of HF, a method for safely recovering and reusing the HF present in the ASO is desirable. The present invention provides closed loop processes for accomplishing this goal.

BACKGROUND ART

U.S. Pat. NO. 2,419,558 discloses a process for recovering fluorine in the form of hydrofluoric acid from a defluorination agent. The defluorinating agent of choice is dehydrated bauxite. Regeneration and recovery of the HF is achieved by passing steam through the defluorinating agent followed by contacting the steam/HF mixture with a metal fluoride. The HF reacts with the metal fluoride to form a complex salt which is then removed and heated to release anhydrous HF.

U.S. Pat. No. 3,976,447 provides a process for absorbing HF from gaseous streams generated by manufacturing processes. The process utilizes alkaline earth metal compounds of calcium, barium and strontium chlorides and fluorides in their anhydrous forms. Regeneration of the absorbent and recovery of the HF is achieved by heating the absorption column to around 225° F. to 350° F. Alternatively, the HF may be recovered by passing a hot gas through the solids.

U.S. Pat. No. 4,199,409 provides a process for separating HF from ASO generated by an HF alkylation unit. The process utilizes a cooler which lowers the temperature of the bottoms produced by the alkylation process. Once the bottoms have been cooled, the mutual solubilities of the ASO and the HF are greatly reduced, resulting in a heavy HF oil phase and a lighter ASO phase. The two phases are then separated and recovered.

GENERAL DISCLOSURE OF THE INVENTION

In general, the present invention provides a process for separating hydrogen fluoride (HF) from acid soluble oils (ASO) generated by acid recovery system of an HF alkylation unit known as an acid rerun column. The process contacts the ASO containing HF stream generated by the alkylation unit with water, in order to form an organic hydrocarbon phase and an aqueous phase containing substantially all of the HF. The phases are separated and the aqueous HF containing phase is passed, either in a liquid or vapor state, through a bed of NaF, to form salts having the general formula of NaF.nHF according to the reaction $nHF + NaF \rightarrow NaF.nHF$. The flow of the aqueous HF containing phase into the NaF bed continues until the presence of HF is detected in the effluent stream. Detection of HF in the effluent stream indicates exhaustion of the bed; however, once flow of the HF has been stopped the bed may be regenerated by reversing the above reaction. The washed ASO can then be neutralized with caustic and reprocessed in refining slop oil streams.

Regeneration of the exhausted NaF bed recovers anhydrous HF for reuse in HF alkylation units and allows reuse of the NaF bed. The bed of NaF.nHF is regenerated by first drying the bed by passing a warm gas inert to HF, NaF and the NaF.nHF salt, through the bed at a temperature of about 95° F. (35° C.) to about 150° F. (65° C.) to remove any remaining water, without removing the HF from the salt. After drying, a hot dry carrier gas, also inert to the constituents of the bed, is passed through the bed at a temperature of about 500° F. (260° C.) to about 610° F. (320° C.) in order to decompose the NaF.nHF salt to NaF with the release of anhydrous HF. The heat from the carrier gas reverses the initial reaction, releasing the anhydrous HF from the salt. During regeneration, it is convenient to maintain conditions which will allow the condensation of the evolving anhydrous HF as it returns to the alkylation unit.

Concisely, the present invention provides a refining process for recovering HF from ASO generated by the HF rerun column of an HF alkylation unit. The process is initiated by removing the ASO containing HF from the rerun column and contacting it with water. The water extracts the HF from the ASO resulting in a system having two phases, an aqueous HF containing phase and an organic phase. Following separation of the phases, caustic treatment of the organic phase neutralizes any remaining HF in the washed ASO, allowing the ASO to be used in other refining processes.

After phase separation, the aqueous HF containing phase passes through a bed of fluidized NaF crystals, where the NaF reacts with the HF to form salts having the general formula NaF.nHF. Passage of the aqueous HF containing phase through the bed in the liquid state can result in some degradation of the NaF bed due to its solubility in water, although desired results will still be obtained. Preferably, as a means of avoiding bed degradation, the bed will be fluidized by passing the aqueous HF containing phase through the bed in the vapor state. In order to maintain the aqueous HF containing phase in the vapor state during the reaction of the HF with the NaF, the temperature of the bed may be altered as necessary depending on the flow rate and the pressure within the bed. Flow of the aqueous HF containing phase to the bed continues until exhaustion of the bed, as determined by the detection of HF in the effluent. After exhaustion of the bed, the process provides for the regeneration of the bed and release of anhydrous HF as previously described.

Thus, the present invention provides environmentally safe processes for recovering HF from hydrocarbon streams generated by an HF alkylation unit and reusing the HF in the alkylation unit.

Further, the present invention provides a process wherein all components of the system are either recycled or reused without producing additional waste requiring subsequent treatment.

BRIEF DESCRIPTION OF THE DRAWING

The drawing is a flow diagram indicating the flow of waste from the acid rerun column to the apparatus of the present invention.

DETAILED DESCRIPTION OF THE INVENTION

Figure 1:
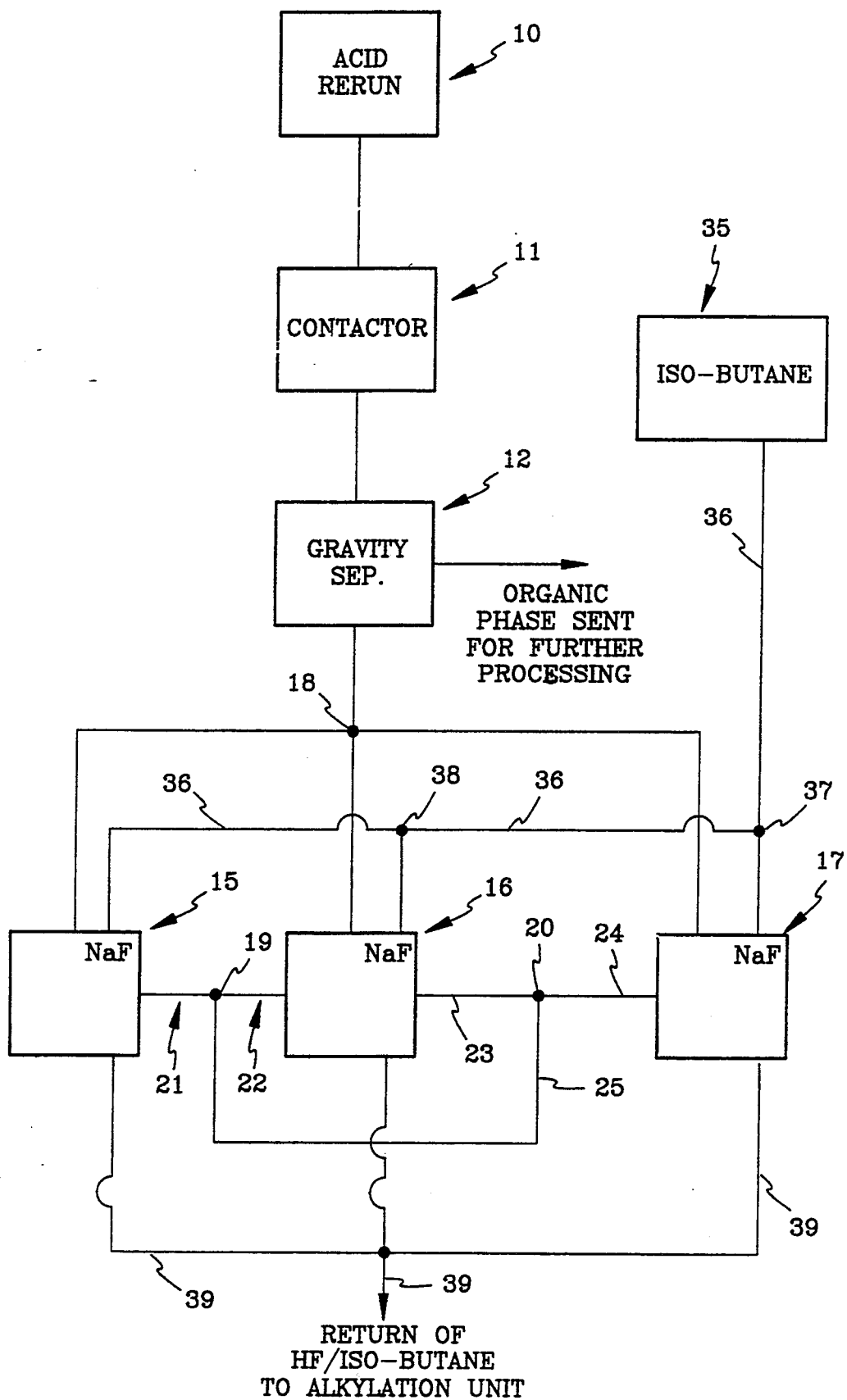

The preferred embodiment of the present invention will utilize at least three beds of NaF, and is illustrated by FIG. 1. Each of the beds are staged sequentially through the processes: in the first stage, the bed functions as the guard bed for the on-line HF-absorption bed; in the second stage, the bed functions as the on-line HF-absorption bed, and in the third stage the bed undergoes regeneration. Additionally, the present process will normally utilize a contactor and a gravity separator. The contactor will be suitable for contacting the waste stream from the acid rerun column of an alkylation unit with water and the separator will be capable of separating fluid mixtures.

In order to better understand the process of the current invention, reference may be made to the accompanying drawing, FIG. 1. First, the ASO waste stream containing HF from the acid rerun unit 10 is contacted with water in a contactor 11. The water extracts all or nearly all (over 99%) of the HF from the ASO. The stream now comprises two phases, an organic hydrocarbon phase and an aqueous HF containing phase. The stream then passes to a gravity separator 12 where the two phases are separated.

Following separation, the organic hydrocarbon phase is treated with caustic to neutralize any remaining acid and sent for further refining. As the process of the current invention is capable of recovering over 99% of the HF in the ASO, caustic usage is greatly reduced. In turn, waste products requiring handling and disposal are also reduced and the time span between replenishment of HF catalyst inventory is greatly increased.

The aqueous HF containing phase is directed to one of at least three NaF beds 15, 16 and 17 through a valve 18. (Beds 15–17 are connected by valves 19, 20 and conduits 21, 22, 23, 24 and 25 in a manner to allow each bed to serve as a reaction or guard bed.) On entering NaF bed 15, the HF within the stream reacts with the NaF to form salts having the general formula of NaF.nHF. Preferably, the aqueous HF containing stream enters reaction bed 15 at a rate sufficient to fluidize the bed. Effluent from bed 15 passes to a second NaF bed 16, through conduits 21, 22 and valve 19, which serves as a guard bed to react with any HF which may break through reaction bed 15.

Flow of the aqueous HF containing phase to reaction bed 15 continues until HF is detected in the effluent stream or the molar amount of HF reacted is about 0.8 times the molar amount of the NaF in the bed 15. (Limiting the reaction of HF to 0.8 times the molar amount of NaF precludes the formation of NaF.nHF with an $n \geq 2$. Salts having an $n \geq 2$ are difficult to fluidize due to their lower melting points and higher densities, leading to a fouling of the bed and incomplete regeneration.) On detection of either of these conditions, flow of the aqueous HF containing phase to reaction bed 15 is halted as reaction bed 15 is now depleted. If an additional bed of NaF 17 is available, the flow of aqueous HF is then redirected to guard bed 16, which then becomes the reaction bed; and, the third bed of NaF 17 becomes the new guard bed.

Upon exhaustion of reaction bed 15 and halting of the flow of the aqueous HF containing phase, the regeneration process is carried out. The regeneration of the NaF bed requires the reversal of the initial reaction process which formed the salts now within the bed. This process requires the elimination of all moisture from the bed, followed by heating the bed to release anhydrous HF.

Drying the salts may be performed in several ways. For example, the salts may be removed from the reaction vessel, filtered and then heated to a temperature between about 95° F. (35° C.) to about 150° F. (65° C.) to drive off the moisture. The temperature for drying is limited at this step in order to preclude the premature release of HF. More preferably, the salts are dried by passing a gas, obtained from storage 35, which is inert to HF, NaF and the salts, through the bed by means of conduit 36 at a temperature of about 95° F. (35° C.) to about 150° F. (65° C.). Flow of the gas is controlled by valves 37 and 38. While the preferred gas is isobutane, other gases suitable for drying the salts include air, methane, ethane, propane, n-butane, nitrogen and the noble gases. If necessary, the drying step may be preceded by a solvent wash in order to remove any residual hydrocarbon.

After the salts are dry, the bed is regenerated by passing a hot carrier gas, inert to HF, NaF and the salts, also obtained from storage 35, through the bed at a temperature of from about 500° F. (260° C.) to about 610° F. (320° C.) to release and entrain anhydrous HF within the carrier gas. Preferably, the hot carrier gas will be isobutane, as isobutane containing HF is a preferred feedstream for the alkylation unit and may be reused immediately as "make-up" HF in the alkylation unit. Nitrogen, air, methane, ethane, propane, n-butane and the noble gases may also be used as carrier gases, but will require separation before the recovered HF may be used in the alkylation unit.

Passing the hot carrier gas through the bed at a temperature of at least 500° F. (260° C.) reverses the initial reaction and evolves anhydrous HF as a gas. By maintaining sufficient pressure within the system the HF/isobutane stream is condensed to a liquid which may then be fed back to the alkylation unit by means of a conduit 39. Once regenerated, the bed serves either as a guard bed or a reaction bed as needs dictate. In this manner each component of the HF recovery process is recycled for use either in the alkylation of olefins, the recovery of HF or as feed for other refining processes.

Waste is greatly reduced, while operating costs and waste disposal costs are minimized.

EXAMPLE 1

Under ideal conditions, the design of a typical HF alkylation unit allows for the loss of about 0.08 lbs. of HF acid catalyst for each barrel (bbl, equivalent to 42 gallons) of alkylate produced. The expected HF losses result from the formation of organic fluorides which leave with the propane, butane, and alkylate product streams and from venting, draining, and sampling losses, as well as from the bottom product of the rerun column. For an "ideal" alkylation unit producing 12,000 bbl/day alkylate, the expected loss of acid is about 960 lb./day due to the formation of organic fluorides. One skilled in the art, will recognize that results of this nature may only be achieved by operating the "ideal" unit with a hydrocarbon feed stream to the reactor having an isobutane to olefin ratio of 13 to 1, less than 20 parts per million by weight (ppmw) of sulfur and approximately 1 ppmw of water. The temperature of the reaction zone should be between about 80° F. (26° C.) and about 100° F. (38° C.), and the HF acid catalyst should have approximately the following composition:

| Component | Wt % |
|---|---|
| HF | 88.0 |
| $H_2O$ | 1.0 |
| Heavy. ASO | 5.0 |
| Dissolved Propane, Butanes, and Alkylate | 6.0 |

For this example, the olefin feed contains the following amounts of propane and normal butane which are removed as products from the fractionation system:
— 2000 bbl/day Propane (99.5 liq. vol. % propane, 0.01 LV % ethane 0.04 LV % iso butane)
— 1000 bbl/day Butane (95 LV % n-butane, 4 LV % iso butane, 1 LV % pentanes)

The propane and butane streams leave the fractionation section containing 400 ppmw fluoride content and the alkylate product leaves the fractionation section containing 250 ppmw fluorides. For this example, losses of HF to vents, drains, or sampling are assumed to be negligible. Therefore, the HF lost as fluorides in the product streams is:

| Propane | 141.6 lb/day |
|---|---|
| Butanes | 81.6 lb/day |
| Alkylate | 736.8 lb/day |
| Total | 960.0 lb/day |

Under these "ideal conditions", the HF lost to rerun bottoms should be 0 lb/day. However, due to the presence of water in the olefin feed stream, the rerun tower must be operated occasionally to eliminate some of the accumulated water. Thus, an azeotrope of water and HF leaves the rerun column bottoms containing 38 wt% HF and the balance water.

Therefore, given conditions where an olefin feed enters the reaction zone at a rate of about 12,000 bbl/day with 1 ppmw of water and assuming an anhydrous isobutane feed, the water rejection requirement is 2.4 lb/day. At this rate, 1.5 lb/day of HF is lost when it forms an azeotrope with the water in the olefin feed. The amount of HF recoverable under these conditions is about 1.5 lb/day at a value of $1.05/day, given an HF price of $1400/ton HF. Thus, for an ideal unit, there is little justification for HF recovery from this stream. The HF can be converted to calcium fluoride solid, producing 6.2 lb/day of solid waste and occupying about 0.03 cu. yards of landfill space.

EXAMPLE 2

In contrast to Example 1, the following example typifies an actual alkylation unit's operating conditions. In this example, the feed rates, product rates and product fluoride contents are the same as the "ideal" case and the assumption that losses due to venting, etc. are negligible is maintained. However, some of the operational variables are changed to reflect more typical operating conditions. For this case, the olefin feed contains between 20 and 150 ppmw of sulfur. The volume ratio of isobutane to olefin entering the reaction zone is 9 to 1 and the reaction zone temperature is between about 100° F. (38° C.) and about 105° F. (41° C.). Under these conditions, the unit produces a considerable amount of light ASO. If the light ASO is not removed from the acid by using the rerun column, the acid strength will decrease rapidly which could result in an acid runaway.

Because of the difficulty in separating light ASO from HF in the rerun column, the alkylation unit must operate the rerun column at a lower acid feed temperature than recommended for removing only heavy ASO from the HF. This results in the loss of some HF from the bottom of the rerun column as a portion of the light ASO containing HF remains with the heavy ASO of the bottom waste product. Of course, the HF lost from the rerun column bottoms must be replaced in the inventory of HF catalyst in the reactor/settler unit. The rerun operating conditions for this example are:

| Pressure | 134 psia |
|---|---|
| Temperature | |
| Acid Feed | 124° C. |
| Top | 115° C. |
| Bottoms | 113° C. |
| Stripping-Isobutane | 177° C. |
| Flow | |
| Acid Feed | 700 bbl/day |
| Stripping-Isobutane | 400 bbl/day |
| Rerun-Bottoms | 50 bbl/day |

The rerun bottoms contain about 20 vol % pure HF (10 bbl/day or 3399 lb/day). The cost of replacing this HF acid would be $2379/day at an HF cost of $1400/ton. A solid waste containing 13,270 lb/day of calcium fluoride is generated occupying a minimum of 2.5 cu. yards in a landfill in addition to those losses due to the formation of organic fluorides which will occur even under ideal circumstances, as previously demonstrated.

In order to produce the calcium fluoride from the HF in the rerun bottoms, the rerun bottoms are neutralized with a caustic solution. The neutralized oil is separated from the caustic and is routed to another refinery process, for example a coker or a slop oil stream. Once the caustic has been depleted to a specified concentration, it is withdrawn from the neutralizing vessel into a tank. In the tank, calcium hydroxide is added to the caustic from the neutralizer. Calcium fluoride precipitates from solution and the caustic is reformed as shown in the equation below:

$$Ca(OH)_2 + 2\ KF \rightarrow CaF_2 + 2\ KOH$$

When virtually all the fluoride has reacted and precipitated, the caustic is pumped back to the neutralizer. The calcium fluoride must then filtered to remove most of the remaining liquid, followed by neutralization of the filter cake in order to meet the pH requirements for non-hazardous landfill disposal. This wet cake has a typical disposed volume of 5 cu. yards/day and occupies more space than the pure calcium fluoride. This operation costs about $1.6 million/yr, including the expense of make-up HF acid, for this one unit.

Through the process of the current invention, about 99 wt % of the HF in the rerun bottoms stream may be recovered in the water/rerun bottoms contactor. The oil would then go to the neutralization unit for removal of the remaining 1 wt. % of HF followed by processing in a slop oil stream. Accordingly, the cost of neutralization, make-up HF acid, and disposal for this unit decreases by 99% to $16,000/yr versus $1.6 million. The amount of solid waste generated also drops from 5 cu. yards/day to 0.05 cu. yards/day.

Alternate Embodiments

While the present invention has been described as a preferred embodiment utilizing three beds of NaF, other arrangements are contemplated. For example, batch type treatment of the ASO containing HF may be accomplished by use of a single NaF bed. Further, other combinations may include one, two or even more than three beds, as required by the particular facility.

A two bed system may be a cost effective alternative to the preferred three bed system. A two bed system may be used in different manners. For example, in a two bed system, one may choose to forego the use of a guard bed and subsequently neutralize any acid which breaks through the reaction bed. Alternatively, one may lengthen or shorten the bed life by adjusting the flow rate of aqueous HF or ASO containing HF into the reaction bed such that a newly regenerated bed is available to serve as a guard bed prior to break through of the acid. In this method, it is envisioned that control of the bed life in the first bed will allow sufficient time for the second bed to be regenerated, according the process previously described, prior to breakthrough of any HF. Once the bed is regenerated, it may then serve as a guard bed until the initial bed is exhausted. Upon exhaustion of the initial bed the second bed becomes the reaction bed and the initial bed is regenerated. Thus, the two beds are cycled between reacting, regenerating and guarding.

In a single bed system, a surge tank is employed to accumulate ASO containing HF until bed regeneration is completed.

Other embodiments will be apparent to those skilled in the art from a consideration of this specification or practice of the invention disclosed herein. It is intended that the specification be considered as only exemplary, with the true scope and spirit of the invention being indicated by the following claims.

We claim:

1. A process for recovering HF from acid soluble oils (ASO) generated by the HF regeneration unit of an HF alkylation unit comprising:
   a) contacting the ASO with water in order to form a hydrocarbon phase and an aqueous HF containing phase,
   b) separating the aqueous HF containing phase from the hydrocarbon phase,
   c) contacting said aqueous HF containing phase with at least one bed of NaF crystals in order to form salts of NaF and HF followed by,
   d) regenerating said bed of NaF with release of anhydrous HF
   e) condensing the released anhydrous HF.

2. The process of claim 1, wherein said process for recovering HF utilizes at least two beds of NaF, the first bed reacting with the aqueous HF containing phase while the second bed is regenerated to release anhydrous HF.

3. The process of claim 1, wherein said process utilizes at least three beds of NaF, a first bed reacting with said aqueous HF containing phase, a second bed acting as a guard in order to react with any HF which breaks through said first bed and a third bed which is being regenerated with release of anhydrous HF, said beds being cycled from reacting to regenerating to guarding as required.

4. The process of claim 1, wherein said aqueous HF containing phase enters said bed at a rate sufficient to fluidize said bed of NaF.

5. The process of claim 1, wherein said regeneration step includes passing a gas, which is inert with respect to the salt, through the salt, at a temperature which is warm enough to remove any moisture, followed by passing another gas, which inert with respect to the salt, through the bed, at a temperature which is hot enough to release anhydrous HF from the salt.

6. The process of claim 5, wherein said gas is selected from the group of nitrogen, air, methane, ethane, propane, iso-butane, n-butane and the noble gases.

7. The process of claim 6, wherein said warm gas is at a temperature of at least about 95° F. and said hot gas is at a temperature of at least about 500° F.

8. The process of claim 1, wherein said aqueous HF containing phase is atomized prior to contacting said bed of NaF.

9. The process of claim 1, wherein said aqueous HF containing phase is vaporized prior to contacting said bed of NaF.

10. In a refinery operation for alkylating olefins through contacting said olefins with HF and recovering HF from the alkylate product by use of an acid regeneration column which also produces acid soluble oils (ASO) containing HF, a process for recovering HF from the ASO comprising:
   a) contacting the ASO containing HF with water in order to form an organic hydrocarbon phase and an aqueous HF containing phase,
   b) separating the aqueous HF containing phase from the organic phase,
   c) treating the organic phase with caustic to neutralize any remaining acid
   d) recovering the neutralized organic phase for use in further refining processes, while
   e) contacting said aqueous HF containing phase with at least one bed of NaF crystals at a temperature and pressure sufficient to maintain said aqueous HF containing phase in the vapor state in order to form salts of NaF and HF followed by,
   f) regenerating said bed of NaF with release of anhydrous HF
   g) recovering the released anhydrous HF, and h) returning said recovered anhydrous HF to the alkylation unit for reuse as a catalyst in the alkylation process.

11. The process of claim 10, wherein said process for recovering HF utilizes at least two beds of NaF, the first bed reacting with the aqueous HF containing phase while the second bed is regenerated to release anhydrous HF.

12. The process of claim 10, wherein said process utilizes three beds of NaF, a first bed reacting with said aqueous HF containing phase, a second bed acting as a guard in order to react with any HF which may breakthrough said first bed and a third bed which is being regenerated with release of anhydrous HF, said beds being cycled from reacting to regenerating to guarding as required.

13. The process of claim 10, wherein said aqueous HF containing phase enters said bed at a rate sufficient to fluidize said bed of NaF.

14. The process of claim 10, wherein said regeneration step includes passing a gas, which is inert with respect to the salt, through the bed at a temperature sufficient to remove any moisture, followed by passing a another gas, which is inert with respect to the salt, through the bed, at a temperature which is hot enough to release anhydrous HF from the salt.

15. The process of claim 14, wherein said gas is selected from the group of nitrogen, air, methane, ethane, propane, iso-butane, n-butane and the noble gases.

16. The process of claim 15, wherein said warm gas is at a temperature of at least about 95° F. and said hot gas is at a temperature of at least about 500° F.

17. The process of claim 10, wherein said aqueous HF containing phase is atomized prior to contacting said bed of NaF.

18. The process of claim 10, wherein said aqueous HF containing phase is vaporized prior to contacting said bed of NaF.

19. The process of claim 10, wherein the flow of aqueous HF containing phase to said bed of NaF is stopped upon detection of HF in the effluent from said bed.

20. The process of claim 12, wherein the flow of aqueous HF containing phase to said bed of NaF is stopped upon detection of reaction products upstream of said guard bed.

21. The process of claim 11, wherein the flow of aqueous HF containing phase to said first bed of NaF is stopped upon detection of reaction products within the effluent of said first bed.

22. In an alkylation process wherein olefins are contacted with HF to yield an alkylate product containing HF, wherein HF is recovered from the alkylate product by use of an acid regeneration column which also produces acid soluble oils (ASO) containing HF, the improvement comprises:

a) contacting the ASO with water in order to form an organic phase and an aqueous HF containing phase, b) separating the aqueous HF containing phase from the hydrocarbon phase, c) contacting said aqueous HF containing phase with at least one bed of NaF in order to form salts of NaF and HF followed by, d) regenerating said bed of NaF with release of anhydrous HF e) condensing the released anhydrous HF.

23. The process of claim 22, wherein said aqueous HF containing phase enters said bed at a rate sufficient to fluidize said bed of NaF.

24. The process of claim 22, wherein said regeneration step includes passing a gas, which is inert with respect to the salt, through the salt, at a temperature that is warm enough to remove any moisture, followed by passing another gas, which inert with respect to the salt, through the bed, at a temperature which is hot enough to release anhydrous HF from the salt.

25. The process of claim 24, wherein said gas is selected from the group of nitrogen, air, methane, ethane, propane, iso-butane, n-butane and the noble gases.

26. The process of claim 25, wherein said warm gas is at a temperature of at least about 95° F. and said hot gas is at a temperature of at least about 500° F.

* * * * *

UNITED STATES PATENT AND TRADEMARK OFFICE
CERTIFICATE OF CORRECTION

PATENT NO. : 5,336,832
DATED : August 9, 1994
INVENTOR(S) : Alfred E. Keller, et. al.

It is certified that error appears in the above-indentified patent and that said Letters Patent is hereby corrected as shown below:

On the Title page, item [75], inventor: "Craig T. Barker, Helsinki, Finland" should be included as an inventor.

Signed and Sealed this

Eleventh Day of October, 1994

Attest:

BRUCE LEHMAN

*Attesting Officer*           *Commissioner of Patents and Trademarks*